US011053176B2

(12) United States Patent
Chen et al.

(10) Patent No.: US 11,053,176 B2
(45) Date of Patent: Jul. 6, 2021

(54) PROCESS FOR CO-PRODUCTION OF MIXED XYLENES AND HIGH OCTANE $C_{9+}$ AROMATICS

(71) Applicant: ExxonMobil Chemical Patents Inc., Baytown, TX (US)

(72) Inventors: Tan-Jen Chen, Seattle, WA (US); Wenyih F. Lai, Bridgewater, NJ (US); Anthony Go, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/979,751

(22) PCT Filed: Mar. 15, 2019

(86) PCT No.: PCT/US2019/022387
§ 371 (c)(1),
(2) Date: Sep. 10, 2020

(87) PCT Pub. No.: WO2019/190774
PCT Pub. Date: Oct. 3, 2019

(65) Prior Publication Data
US 2021/0040016 A1 Feb. 11, 2021

Related U.S. Application Data

(60) Provisional application No. 62/650,673, filed on Mar. 30, 2018.

(30) Foreign Application Priority Data

Apr. 27, 2018 (EP) ..................... 18169815

(51) Int. Cl.
*C07C 2/00* (2006.01)
*C07C 2/86* (2006.01)
(Continued)

(52) U.S. Cl.
CPC ............... *C07C 2/865* (2013.01); *B01J 29/18* (2013.01); *B01J 29/7007* (2013.01);
(Continued)

(58) Field of Classification Search
CPC .......... C07C 6/126; C07C 15/02; C07C 2/66; C07C 2/864; C07C 5/2729; C07C 15/073;
(Continued)

(56) References Cited

U.S. PATENT DOCUMENTS

| 4,211,886 A * | 7/1980 | Tabak ................. C07C 4/12 585/321 |
| 2015/0141700 A1* | 5/2015 | Johnson ............... C07C 2/864 568/385 |

FOREIGN PATENT DOCUMENTS

| CN | 104445262 | 3/2015 |
| GB | 1403329 | 8/1975 |
| WO | 2018/067281 | 4/2018 |

* cited by examiner

*Primary Examiner* — Sharon Pregler

(57) ABSTRACT

Disclosed is a process for producing mixed xylenes and $C_{9+}$ hydrocarbons in which an aromatic hydrocarbon feedstock comprising benzene and/or toluene is contacted with an alkylating agent comprising methanol and/or dimethyl ether under alkylation conditions in the presence of an alkylation catalyst to produce an alkylated aromatic product stream comprising the mixed xylenes and $C_{9+}$ hydrocarbons. The mixed xylenes are subsequently converted to para-xylene, and the $C_{9+}$ hydrocarbons and its components may be supplied as motor fuels blending components. The alkylation catalyst comprises a molecular sieve having a Constraint Index in the range from greater than zero up to about 3. The molar ratio of aromatic hydrocarbon to alkylating agent is in the range of greater than 1:1 to less than 4:1.

19 Claims, 1 Drawing Sheet

(51) Int. Cl.
*B01J 29/18* (2006.01)
*B01J 29/70* (2006.01)
*B01J 35/10* (2006.01)
*C07C 5/27* (2006.01)
*C10L 1/06* (2006.01)
*C10L 10/10* (2006.01)

(52) U.S. Cl.
CPC ....... *B01J 29/7034* (2013.01); *B01J 35/1019* (2013.01); *C07C 2/864* (2013.01); *C07C 5/2737* (2013.01); *C10L 1/06* (2013.01); *C10L 10/10* (2013.01); *C07C 2529/18* (2013.01); *C07C 2529/70* (2013.01); *C10L 2290/24* (2013.01)

(58) Field of Classification Search
CPC ......... C07C 15/08; C07C 15/085; C07C 7/10; C10G 21/00; C10G 2300/1044; C10G 2400/30; C10G 29/205; C10G 45/00; C10G 69/06
See application file for complete search history.

PROCESS FOR CO-PRODUCTION OF MIXED XYLENES AND HIGH OCTANE $C_{9+}$ AROMATICS

CROSS REFERENCE TO RELATED APPLICATION

This application is a U.S. national phase application of PCT application No. PCT/US2019/022387 having a filing date of Mar. 15, 2019, which claims priority to and the benefit of U.S. provisional application Ser. No. 62/650,673 having a filing date of Mar. 30, 2018 and European Application No. 18169815.0 having a filing date of Apr. 27, 2018, the contents of all of which are hereby incorporated by reference in their entirety.

FIELD

This disclosure relates to a process for producing mixed xylenes and $C_{9+}$ hydrocarbons by the alkylation of an aromatic hydrocarbon stream comprising benzene and/or toluene with a stream comprising methanol and/or dimethyl ether in the presence of a molecular sieve having a Constraint Index in the range from greater than zero up to about 3, most preferably, ZSM-12.

BACKGROUND

Recent discoveries and increasing production of shale gas represent a significant new source of natural gas (essentially methane). As a result, natural gas supply has become less expensive and more abundant, making it an advantageous feedstock to upgrade. This has led to the development of processes for converting natural gas to methanol as an intermediate for the production of aromatic-rich feeds.

The refining industry currently formulates the motor gasoline pool by blending a wide range of hydrocarbon streams including monocyclic aromatic compounds and $C_4$ to $C_{10}$ saturated branched acyclic alkanes and olefins. However derived, these hydrocarbon streams contain a broad range of components and have usually been processed in unit operations (e.g., by hydrocarbon conversion, distillation, or solvent extraction), to obtain specific desired components or combinations of components. One purpose of these operation is to obtain high octane gasoline components such as $C_9$ and $C_{10+}$ aromatic hydrocarbons. Another purpose of these operations is to obtain high purity, often greater than 99%, chemical feed stocks such as para-xylene from mixed xylenes, which have been used in huge quantities in the manufacture of styrene, phenol, polyamide monomers, terephthalic acid and other chemical products.

There is therefore a need for an improved process for the production of high octane motor gasoline blending components and mixed xylenes, such as for example, by the alkylation of benzene and/or toluene with methanol and/or dimethyl ether. This disclose meets this and other needs.

SUMMARY

In an aspect of this disclosure, an aromatic hydrocarbon feed may be converted to an alkylated aromatic product stream via an alkylation reaction with an alkylating agent stream under alkylation conditions in the presence of an alkylation catalyst to form an alkylated aromatic product stream. The alkylated aromatic product stream formed by the alkylation reaction comprises mixed xylenes and $C_{9+}$ hydrocarbons. The aromatic hydrocarbon feed may comprise toluene and/or benzene, and the alkylating agent comprises methanol and/or dimethyl ether.

In this disclosure, the alkylation catalyst comprises a molecular sieve, preferably a relatively large pore molecular sieve, more preferably, a molecular sieve having a Constraint Index in the range from greater than zero up to about 3, from greater than zero up to about 2, and most preferably, a Constraint Index of about 2. In the alkylation reaction, the molar ratio of aromatic hydrocarbon to alkylating agent is selected from a range of from about 1:1 up to about 4:1; preferably, of from about 2:1 to less than about 4:1; more preferably, the molar ratio of aromatic hydrocarbon to alkylating agent is about 3:1.

The alkylated aromatic product stream may comprise at least 60 wt %, preferably at least 70 wt % of mixed xylenes, and comprises at least 17 wt %, preferably at least 21 wt % of $C_{9+}$ aromatic hydrocarbons, based on the weight of the alkylated aromatic product stream.

The mixed xylenes and $C_{9+}$ hydrocarbons may be recovered from said alkylated aromatic product. The mixed xylenes may be supplied to a xylenes isomerization unit to produce para-xylene. The $C_{9+}$ hydrocarbon may be supplied to a separation unit to recover at least a $C_9$ aromatic hydrocarbon stream which comprises at least a mixture of trimethylbenzene and a mixture of ethylmethylbenzenes. The $C_9$ aromatic hydrocarbon stream may be separated in the separation unit to recover a stream which comprise at least a mixture of trimethylbenzene and a stream which comprises at least a mixture of ethylmethylbenzenes. These trimethylbenzene and ethylmethylbenzene streams may be supplied together or separately as motor fuels blending component(s), preferably, having a high MONC and RONC values.

Advantageously, the alkylation catalyst comprises a molecular sieve having a framework structure of MTW, a BEA*, a FAU. The molecular sieve may be a zeolite and/or a mixture of these framework structures. Preferably, the molecular sieve of MTW framework structure is ZSM-12. The molecular sieve of BEA* framework structure is preferably, zeolite Beta. The molecular sieve of FAU framework structure is preferably zeolite Y or Ultrastable Y (USY). Preferably, the molecular sieve of MOR framework structure is natural Mordenite or TEA-Mordenite. In some aspects, the molecular sieve is selected from the group consisting of ZSM-3, ZSM-4, ZSM-14, ZSM-18, ZSM-20, ZSM-38 and mixtures thereof.

Conveniently, the alkylation conditions are relatively mild, preferably the reaction is carried out under alkylation conditions of a temperature in the range of less than 500° C., preferably in the range of from 300° C. to 450° C. The pressure is in the range from 700 kPa-a to 7000 kPa-a. The weight hourly space velocity based on the aromatic hydrocarbon feed is in the range of 50 $hr^{-1}$ to 0.5 $hr^{-1}$.

In another aspect of this disclosure, an aromatic hydrocarbon feed may be converted to an alkylated aromatic product stream which comprise $C_9$ aromatic hydrocarbons and $C_{10}$ aromatic hydrocarbons via an alkylation reaction with an alkylating agent stream under alkylation conditions in the presence of an alkylation catalyst, preferably, ZSM-12, to form an alkylated aromatic product stream. The alkylated aromatic product stream formed is separated into a $C_9$ aromatic hydrocarbon stream and, optionally, a $C_{10}$ aromatic hydrocarbon stream each of which may be supplied as a motor fuels blending component.

The $C_9$ aromatic hydrocarbon stream comprises a mixture of trimethylbenzenes and/or a mixture of ethylmethylbenzenes, which may be separated and also supplied as a motor fuels blending component. The trimethylbenzenes are isomers which comprises and includes 1,2,4-trimethylbenzene, 1,3,5-trimethylbenzene and 1,2,3-trimethylbenzene. The ethylmethylbenzenes comprises and includes 1-ethyl, 2-methylbenzene and 1-ethyl, 3-methylbenzene. Any of the trimethylbenzene isomers or any of the ethylmethylbenzenes may also be separated and supplied as a motor fuels blending component having a high octane number.

DETAILED DESCRIPTION OF THIS DISCLOSURE

Figure 1:
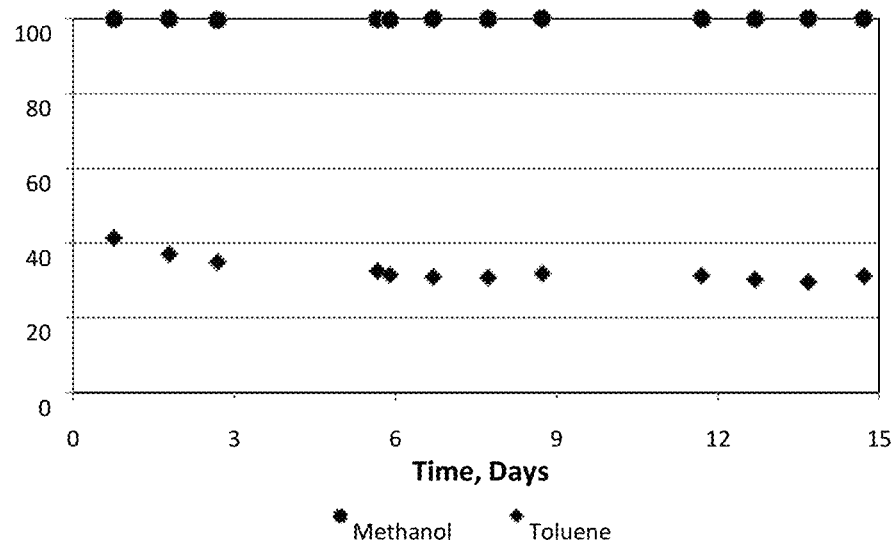
FIG. 1 is a graph of the conversion of toluene and methanol over ZSM-12 against time on stream in the process of alkylating toluene with methanol described in Example 2.

The alkylation processes disclosed herein provide for producing mixed xylenes and $C_{9+}$ aromatic hydrocarbons in the presence of an alkylation catalyst which comprises a relatively large pore molecular sieve, such as, for example, a molecular sieve having a Constraint Index in the range from greater than zero up to about 3. Such molecular sieves include, but are not limited to, molecular sieves which have a MTW, a BEA*, a FAU or a MOR framework structure, and are described further below.

Definitions

As used herein, the term "Alpha Value" means a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference.

As used herein, the terms "aromatics" and "aromatic hydrocarbon" mean a class of hydrocarbon compounds containing at least one aromatic core.

As used herein, the term "hydrocarbon" or "hydrocarbons" means a class of compounds containing a hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, the term "$C_n$" hydrocarbon wherein n is a positive integer, e.g., 1, 2, 3, 4, 5, etc., means a hydrocarbon having n number of carbon atom(s) per molecule.

As used herein, the term "$C_{n+}$" hydrocarbon wherein n is a positive integer, e.g., 1, 2, 3, 4, 5, etc., means a hydrocarbon having at least n number of carbon atom(s) per molecule. Thus, the term "$C_{9+}$ hydrocarbon" means a hydrocarbon having 9 or more carbon atoms, and includes a "$C_{10+}$ hydrocarbon".

As used herein, the term "$C_{n-}$" hydrocarbon wherein n is a positive integer, e.g., 1, 2, 3, 4, 5, etc., as used herein, means a hydrocarbon having no more than n number of carbon atom(s) per molecule.

As used herein, the term "Constraint Index" is a convenient measure of the extent to which an aluminosilicate or molecular sieve provides controlled access to molecules of varying sizes to its internal structure. For example, aluminosilicates which provide a highly restricted access to and egress from its internal structure have a high value for the Constraint Index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218.

As used herein, the term "mixed xylenes" means an equilibrium mixture of ortho-xylene, meta-xylene and para-xylene.

As used herein, the terms "molecular sieve" and "zeolite" may be used interchangeably.

As used herein, the term "MON" means a Motor Octane Number.

As used herein, the term "MONC" means a Motor Octane Number free of lead.

As used herein, the term "RON" means a Research Octane Number.

As used herein, the term "RONC" means a Research Octane Number free of lead.

As used herein, the term "motor fuels blending component" means a hydrocarbon used for blending into a finished motor fuels or gasoline pool having a RONC value in the range of 108 to 119 and/or a MONC value in the range of 98 to 111.

Process

An aspect of this disclosure, is a process in which an aromatic hydrocarbon feed may be converted to an alkylated aromatic product stream via an alkylation reaction with an alkylating agent under alkylation conditions in the presence of an alkylation catalyst, discussed below, which is disposed in at least one alkylation reaction zone(s). The alkylated aromatic product stream is recovered and may be separated as a $C_8$ hydrocarbon stream and a $C_{9+}$ aromatic hydrocarbon stream. The $C_8$ hydrocarbon stream includes, for example, mixed xylenes. The $C_{9+}$ hydrocarbon stream includes, for example, $C_9$ aromatic hydrocarbons, such as, for example, tri-methylbenzenes, and $C_{10}$ aromatic hydrocarbons. The mixed xylenes stream recovered may be isomerized to para-xylene. The $C_{9+}$ aromatic hydrocarbon stream may be supplied to a separation unit to recover at least a $C_9$ aromatic hydrocarbon stream and a $C_{10}$ hydrocarbon stream. The $C_9$ aromatic hydrocarbon stream, discussed below, and, optionally, the $C_{10}$ hydrocarbon stream may be supplied as motor fuels blending components.

The aromatic hydrocarbon feed comprises preferably toluene, or in other aspects, at least 90 wt % toluene, based on the weight of said aromatic hydrocarbon feed, or is toluene alone. Optionally, such toluene feed may be co-fed with benzene. Alternatively, the feed may be benzene alone. The alkylating agent comprises preferably, methanol or as a mixture of methanol and toluene and/or benzene. Optionally, the alkylating agent comprises methanol and/or dimethyl ether or as a mixture of methanol and/or dimethyl ether and toluene and/or benzene.

The process is effective to convert the benzene and/or toluene to mixed xylenes and $C_{9+}$ aromatic hydrocarbons with essentially 100% methanol conversion and substantially no light gas make. The high methanol utilization is surprising in light of the methanol utilization in the prior art toluene and/or benzene methylation processes, and results in the substantial advantages of less coke formation, which increases the catalyst life. Furthermore, in prior art processes, it is preferred to co-feed steam into the reactor with the methanol to minimize the methanol side reactions, and the steam negatively impacts catalyst life. With the nearly 100% of the methanol reacting with aromatic rings to produce aromatics in the inventive process, there is no need to co-feed steam, decreasing the energy demands of the process and increasing catalyst life.

The selectivity to mixed xylenes in aspects disclosed herein is typically on the order of at least 60 wt %, preferably at least 70 wt %, most preferably at least 75 wt % of mixed xylenes, based on the weight of the alkylated aromatic product stream. The by-products are benzene and $C_{9+}$ aromatic hydrocarbons, such as, for example, $C_9$ and $C_{10}$ aromatic hydrocarbons. The $C_{9+}$ aromatic hydrocarbons comprise at least 21 wt %, or least 17 wt %, or at least 15 wt %, based on the weight of the alkylated aromatic product stream. The $C_9$ aromatic hydrocarbons comprises at least 10 wt %, or preferably at least 13 wt %, or more preferably at least 15 wt %, or most preferably at least 17 wt %, based on the weight of the alkylated aromatic product stream. The $C_{10}$ aromatic hydrocarbons comprise at least 4 wt %, or least 3 wt %, or at least 1 wt %, based on the weight of the alkylated aromatic product stream.

The alkylated aromatic product stream produced is recovered as at least a stream comprising mixed xylenes, and at least a stream comprising $C_{9+}$ aromatic hydrocarbons. Such alkylated aromatic product stream also comprises benzene and/or toluene (both residual and coproduced in the process) along with co-produced water, oxygenate by-products, and in some cases, unreacted methanol. It is, however, generally preferred to operate the process so that all the methanol is reacted with the aromatic hydrocarbon feed and the alkylated aromatic product stream is generally free of residual methanol. The alkylated aromatic product stream is also generally free of light gases generated by methanol decomposition to ethylene and other olefins. In some embodiments, the alkylated aromatic product stream may contain up to at least 75 wt % mixed xylenes, based on the weight of the alkylated aromatic product stream, and para-xylenes may comprise at least 35 wt %, based on the weight of the mixed xylenes fraction.

After separation of the water, the alkylated aromatic product stream may be fed to a separation unit or section, such as one or more distillation columns, by conventional distillation techniques to recover by conventional distillation techniques the mixed xylenes and separate the benzene and toluene from the $C_{9+}$ aromatic hydrocarbon by-products. The mixed xylenes stream is supplied to a xylenes isomerization unit to produce para-xylene.

The $C_{9+}$ aromatic hydrocarbons can be separated as a component for blending into motor fuels; preferably, such $C_{9+}$ aromatics have a high octane number, such as a RONC value over 108 and MONC value of over 98. Alternatively, the $C_{9+}$ aromatic hydrocarbons may be transalkylated with additional benzene and/or toluene to make additional mixed xylenes. The benzene may be separated from the alkylated aromatic product stream and recycled back to the alkylation reaction zone(s).

The life of the alkylation catalyst is enhanced as compared with existing processes since methanol decomposition is much less at the lower reaction temperature. Moreover, the use of a larger pore molecular sieve minimizes diffusion limitations and allows the alkylation to be carried out at commercially viable WHSVs. Additionally, when a toluene feed (one having at least 90 wt % of toluene, based on the weight of said aromatic hydrocarbon feed) is used, more alkylating agent reacts with the toluene, versus other molecules such as alkylating agent or by-products of the reaction, to produce mixed xylenes as compared to existing processes.

Oxygenate by-products may be removed from the alkylated aromatic product stream by any means known in the art, such as adsorption as described in U.S. Pat. Nos. 9,012,711, 9,434,661, and 9,205,401; caustic wash as described in U.S. Pat. No. 9,294,962; crystallization as disclosed in U.S. Pat. Nos. 8,252,967, 8,507,744, and 8,981, 171; and conversion to ketones as described in U.S. Patent Publication Nos. 2016/0115094 and 2016/0115103.

The mixed xylenes recovered from the alkylated aromatic product stream and any downstream $C_{9+}$ transalkylation process may be sent to a para-xylene production loop. The latter comprises para-xylene separation section, where para-xylene is conventionally separated by adsorption or crystallization, or a combination of both, and recovered. When para-xylene is separated by adsorption, the adsorbent used preferably contains a zeolite. Typical adsorbents used include crystalline aluminosilicate zeolites either natural or synthetic, such as for example zeolite X, or Y, or mixtures thereof. These zeolites are preferably exchanged by cations such as alkali or alkaline earth or rare earth cations. The adsorption column is preferably a simulated moving bed column (SMB) and a desorbent, such as for example paradiethylbenzene, paradifluorobenzene, diethylbenzene, or toluene, or mixtures thereof, is used to recover the selectively adsorbed para-xylene. Commercial SMB units that are suitable for use in the inventive process are PAREX™ or ELUXYL™.

The alkylation catalyst, discussed below, in one or more aspects of this disclosure, comprises a molecular sieve, preferably a relatively large pore molecular sieve, more preferably, a molecular sieve having a Constraint Index in the range from greater than zero up to about 3.

Another aspect of this disclosure is a process for producing a $C_9$ aromatic hydrocarbon stream and a $C_{10}$ aromatic hydrocarbon stream which comprises a number of steps. An aromatic hydrocarbon feed which comprises benzene and/or toluene is contacting or reacted with a feed which comprises methanol and/or dimethyl ether in the presence of an alkylation catalyst comprising ZSM-12 under alkylation conditions to produce an alkylated aromatic product stream. Alternatively, the process may be fed a mixed feed which comprises a mixture of benzene and/or toluene and and/or dimethyl ether.

The aromatic hydrocarbon feed and the methanol feed is reacted to produce an alkylated aromatic product stream which comprises the $C_9$ aromatic hydrocarbons and $C_{10}$ aromatic hydrocarbons along with unreacted benzene and other by-products. Optionally the methanol feed may be co-fed with dimethyl ether or dimethyl ether may be the feed alone. In the reaction, the molar ratio of aromatic hydrocarbon to methanol feeds is in the range of from greater than about 1:1 to less than about 4:1, preferably from about 2:1 up to about 4:1, more preferably from about 2.5:1 to about 3.5:1, and most preferably about 3:1.

The alkylation conditions comprises a temperature in the range of about 500° C. or less, or in the range from about 300° C. to about 450° C., a pressure in the range of from 700 kPa-a to 7000 kPa-a, and a weight hourly space velocity based on the aromatic hydrocarbon feed of 50 hr$^{-1}$ to 0.5 hr$^{-1}$. In a second step of the process, streams comprising the $C_9$ aromatic hydrocarbon and the $C_{10}$ aromatic hydrocarbon are separated from said alkylated aromatic product stream. These streams may then be supplied as motor fuels blending components. Preferably, such $C_9$ aromatic hydrocarbon and/or $C_{10}$ aromatic hydrocarbon blending components have a high octane number, such as a RONC value in the range of 108 to 111, and MONC value in the range of 98 to 111.

The $C_9$ aromatic hydrocarbon stream may comprise a mixture of trimethylbenzene and a mixture of ethylmethylbenzenes. These mixtures may be supplied to a separation unit or section, such as one or more distillation columns, to recover by conventional distillation techniques, a stream comprising said mixture of trimethylbenzenes and/or a stream comprising a mixture of ethylmethylbenzenes. Such streams may be supplied as motor fuels blending components having a high octane number in the range as stated hereinbefore.

The mixture of trimethylbenzenes may comprise a mixture of trimethylbenzene isomers. Such isomers comprise 1,2,4-trimethylbenzene, 1,3,5-trimethylbenzene and 1,2,3-trimethylbenzene. This mixture of isomers may be supplied as a motor fuels blending component. Alternatively, such mixture may be supplied to a separation unit or section, such as one or more distillation columns, to recover by conventional distillation techniques one or more separate streams comprising 1,2,4-trimethylbenzene, 1,3,5-trimethylbenzene and 1,2,3-trimethylbenzene. Such streams may also be supplied as motor fuels blending components having a high octane number in the range as stated hereinbefore.

The mixture of ethylmethylbenzenes may comprise 1-ethyl, 2-methylbenzene and 1-ethyl, 3-methylbenzene. This mixture may be supplied as a motor fuels blending component. Alternatively, such mixture may be supplied to a separation unit or section, such as one or more distillation columns, to recover by conventional distillation techniques one or more separate streams comprising 1-ethyl, 2-methylbenzene and 1-ethyl, 3-methylbenzene. Such streams may also be supplied as motor fuels blending components having a high octane number in the range as stated hereinbefore.

Alkylation Catalysts

The alkylation catalyst comprises a molecular sieve having a Constraint Index a Constraint Index in the range from greater than zero up to about 3, preferably, from greater than zero up to about 2, and most preferably, a Constraint Index of about 2.

Examples of suitable molecular sieves having a Constraint Index of greater than zero up to about 3 for use in the present process comprise zeolite Beta, zeolite Y, Ultrastable Y (USY), Ultrahydrophobic Y (UHP-Y), Dealuminized Y (Deal Y), Mordenite, ZSM-3, ZSM-4, ZSM-12, ZSM-14, ZSM-18, ZSM-20, ZSM-38 and mixtures thereof.

Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795. Zeolite Y and Mordenite are naturally occurring materials but are also available in synthetic forms, such as TEA-Mordenite (i.e., synthetic Mordenite prepared from a reaction mixture comprising a tetraethylammonium directing agent). TEA-Mordenite is disclosed in U.S. Pat. Nos. 3,766,093 and 3,894,104.

Zeolite ZSM-3 is described in U.S. Pat. No. 3,415,736. Zeolite ZSM-4 is described in U.S. Pat. No. 4,021,947. Zeolite ZSM-12 is described in U.S. Pat. No. 3,832,449. Zeolite ZSM-14 is described in U.S. Pat. No. 3,923,636. Zeolite ZSM-18 is described in U.S. Pat. No. 3,950,496. Zeolite ZSM-20 is described in U.S. Pat. No. 3,972,983. ZSM-38 is described in U.S. Pat. No. 4,046,859, and has a Constraint Index of 2 as stated in U.S. Pat. No. 3,960,705.

The molecular sieve may have a framework structure of MTW, a BEA*, a FAU.

The molecular sieve may be a zeolite and/or a mixture of these framework structures. Preferably, the molecular sieve of MTW framework structure is ZSM-12. The molecular sieve of BEA* framework structure is zeolite Beta. The molecular sieve of FAU framework structure is preferably zeolite Y or Ultrastable Y (USY). The molecular sieve of MOR framework structure is natural Mordenite or TEA-Mordenite.

Additionally or alternatively, the molecular sieves useful herein may be a zeolite characterized by a molar ratio of silicon to aluminum. In particular aspects of this disclosure, the molecular sieves suitable herein include those having a $Si/Al_2$ molar ratio in the range from about 5 to 100, preferably in the range from about 10 to about 80 molar, most preferably, in the range from about 15 to about 50 molar.

The alkylation catalyst has an Alpha Value in the range from 100 to 800, preferably in a range of 150 to 600, most preferably from 200 to 500.

The molecular sieve crystals of the alkylation catalyst has a crystal size in the range of greater than 0.05 micron up to about 0.2 micron or greater than 0.05 microns up to 0.5 microns for the primary crystals.

The above molecular sieves may be used as the alkylation catalyst employed herein without any binder or matrix. Alternatively, the molecular sieves may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Except for such metal oxides, the alkylation catalyst does not contain an added metal, such as for example a rare earth metal or an alkaline earth metal.

Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 wt % and more usually, particularly, when the composite is prepared in the form of beads, in the range of about 2 to about 80 wt % of the composite.

Alkylation Conditions

The present alkylation process is conducted at relatively low temperatures, namely less than 500° C., such as less than 475° C., or less than 450° C., or less than 425° C., or less than 400° C. In order to provide commercially viable reaction rates, the process may be conducted at temperatures of at least 250° C., such as least 275° C., for example least 300° C. In terms of ranges, the process may be conducted at temperatures ranging from 250° C. to less than 500° C., such as from 275° C. to 475° C., for example from 300° C. to 450° C. Operating pressures will vary with temperature but generally are at least 700 kPa-a, such as at least 1000 kPa-a, for example at least 1500 kPa-a, or at least 2000 kPa-a, up to about 7000 kPa-a, for example up to about 6000 kPa-a, up to about 5000 kPa-a. In terms of ranges, operating pressures may range from 700 kPa-a to 7000 kPa-a, for example from 1000 kPa-a to 6000 kPa-a, such as from 2000 kPa-a to 5000 kPa-a. Suitable WHSV values based on total aromatic and alkylating agent feeds are in the range from 50 hr$^{-1}$ to 0.5 hr$^{-1}$, such as in the range from 10 hr$^{-1}$ to 1 hr$^{-1}$. In some aspects of this disclosure, at least part of the aromatic feed, the methanol alkylating agent and/or the alkylation effluent may be present in the alkylation reaction zone(s) in the liquid phase.

Reactor

The alkylation reaction can be conducted in any known reactor system including, but not limited to, a fixed bed reactor, a moving bed reactor, a fluidized bed reactor and a reactive distillation unit. In addition, the reactor may comprise a single reaction zone or multiple reaction zones located in the same or different reaction vessels. In addition, injection of the methanol and/or dimethyl ether alkylating agent can be effected at a single point in the reactor or at multiple points spaced along the reactor.

Feeds

The feeds to the present process comprise an aromatic hydrocarbon feed, comprising benzene and/or toluene, and an alkylating agent comprising methanol, optionally, and/or dimethyl ether. Any refinery aromatic feed can be used as the source of the benzene and/or toluene, although in some aspects of this disclosure it may be desirable to use an aromatic hydrocarbon feed which comprises at least 90 wt % toluene, based on the weight of said aromatic hydrocarbon feed. In addition, in some aspects, it may be desirable to pre-treat the aromatic hydrocarbon feed to remove catalyst poisons, such as nitrogen and sulfur-compounds. In other aspects, the feed may further include non-aromatics, such as a refinery aromatic feed from which the non-aromatics have not been extracted.

The disclosure will now be more particularly described with reference to the following non-limiting Examples and the accompany drawings.

EXAMPLES

X-ray Diffraction Patterns

The X-ray diffraction data (powder XRD or XRD) were collected with a Bruker D4 Endeavor diffraction system with a VÅNTEC multichannel detector using copper K-alpha radiation. The diffraction data were recorded by scanning mode with 0.018 degrees two-theta, where theta is the Bragg angle, and using an effective counting time of about 30 seconds for each step.

Measurement of Total Surface Area and Mesoporous Surface Area by BET

The total BET and the t-Plot micropore surface area were measured by nitrogen adsorption/desorption with a Micromeritics Tristar II 3020 instrument after degassing of the calcined zeolite powders for 4 hours at 350° C. The mesoporous surface area was obtained by the subtraction of the t-plot micropore from the total BET surface area. The mesoporous volume was derived from the same data set. More information regarding the method can be found, for example, in "Characterization of Porous Solids and Powders: Surface Area, Pore Size and Density", S. Lowell et al., Springer, 2004.

Alpha Value

The experimental conditions of the test used herein included a constant temperature of 538° C. and a variable flow rate as described in detail in the Journal of Catalysis, Vol. 61, p. 395 (1980).

Sorption Data

Sorption data for n-hexane adsorption were equilibrium adsorption values determined as using a weighed sample of the calcined adsorbent was contacted with the desired pure adsorbate vapor in an adsorption chamber, evacuated to less than 1 mm Hg and contacted with 40 Torr of n-hexane vapor pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbent.

Example 1

Preparation of ZSM-12 Catalyst

Small crystals of ZSM-12 were synthesized according to the disclosure in the U.S. Pat. No. 8,202,506, incorporated herein by reference. The X-ray diffraction (XRD) pattern of the as-synthesized material showed the typical pure phase of ZSM-12 topology. The SEM of the as-synthesized material shows that the material was composed of agglomerates of small crystals (with an average crystal size of <0.05 microns). The resulting ZSM-12 crystals had a $SiO_2/Al_2O_3$ molar ratio of about 43. Alumina-bound catalysts were formed by extrusion using about 80 wt % of ZSM-12 as-synthesized crystals and about 20 wt % alumina (Versal™ 300, obtainable from Honeywell UOP) to make 1/20" quadrulobe extrudates. The resulting dried extrudates were calcined in nitrogen (for about 3 hours at about 538° C. (1000° F.), ammonium exchanged with about 1N ammonium nitrate solution, and calcined in air (for about 6 hours at 538° C.(1000° F.) to form a finished acidic, designated as H-ZSM-12, as an extrudate in the shaped of a quadrulobe and having an Alpha Value of 540, a hexane sorption of 44.5 mg/g, and surface area of 334 m$^2$/g as measured by BET.

Example 2

Performance Evaluation

An experiment was conducted to investigate the production of mixed xylenes and $C_{9+}$ aromatics by the alkylation of toluene with methanol at a temperature of 350° C., a pressure of 600 psig (4238 kPa-a) and a WHSV of 3.5 hr$^{-1}$ based on total feed. The feed used consisted of a mixture of methanol and toluene in the molar ratio of 3:1. The catalyst used was the H-ZSM-12 (80% zeolite/20% alumina binder), described above, which has a Constraint Index in the range of about 1 to about 3. The reaction was carried out in a down flow fixed bed reactor. The liquid product was collected and analyzed by a 6890 Agilent GC. The gas yield was calculated by difference. The results are summarized in FIG. 1 and FIG. 2.

Methanol and Toluene Conversion

FIG. 1 shows the toluene and methanol conversion over the H-ZSM-12 catalyst in a fifteen (15) day test. As can be seen from FIG. 1, the methanol conversion was essentially 100%. No methanol was detected in the product throughout the run. The toluene conversion was stable over the fifteen day test. The average toluene conversion is over 31%, consistent with the feed composition.

Selectivity

Figure 2:
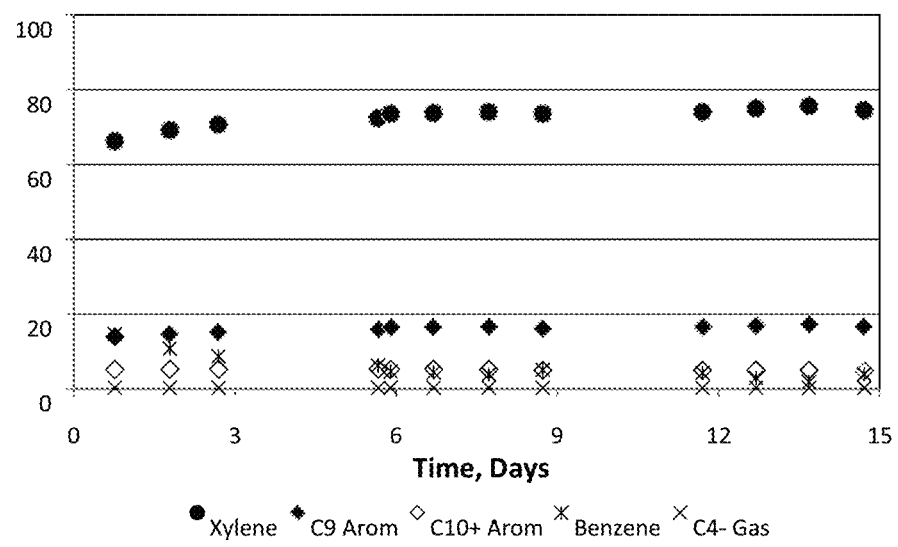
FIG. 2 is a graph of the selectivity of toluene and methanol over ZSM-12 against time on stream in the process of alkylating toluene with methanol described in Example 2.

FIG. 2 shows the selectivity of mixed xylenes, $C_9$, $C_{10+}$, benzene and $C_4$ gas in a fifteen (15) day test. As can be seen from FIG. 2, the average mixed xylenes selectivity started at 65 percent and then increases to 75 percent after the catalyst reached steady state. The average $C_9$ selectivity was 17%. The average $C_{10+}$ selectivity was 4%. The average benzene selectivity was 4 wt %. The gas make was essentially nil.

$C_{9+}$ Aromatics Distribution

The Table displays the makeup of the $C_{9+}$ aromatics produced from alkylation of toluene with methanol over ZSM-12 catalyst. As can be seen from the Table, the $C_9$ aromatics is comprised of 64% of 1,2,4-trimethylbenzene, which has a RONC value of 110 and a MONC of 102.

The $C_9$ aromatics also contain 28% 1,3,5 tri-methylbenzene, which has a RONC value of 119 and MONC of 111. Thus, the trimethylbenzenes have RONC values between 108 and 119 and MONC values between 98 and 111.

The $C_9$ aromatics produced from the alkylation of methanol with toluene is expected to be an excellent blend component for motor fuels (mogas) pool. Some $C_{10+}$ aromatics are also produced when toluene is alkylated with methanol over ZSM-12. The $C_{10+}$ aromatics are also expected to be excellent blending component for mogas.

TABLE $C_{9+}$ Aromatics Composition and Octane Values

| Component | Conc., % | RONC | MONC |
|---|---|---|---|
| 1,2,4-trimethylbenzene | 63.5 | 110 | 102 |
| 1,3,5-trimethylbenzene | 27.5 | 119 | 111 |
| 1,2,3-trimethylbenzene | 8.3 | 108 | 98 |
| 1-ethyl, 2-methylbenzene | 0.5 | 114 | 102 |
| 1 ethyl, 3-methylbenzene | 0.2 | 113 | 102 |

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the example and descriptions set forth herein, but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

All numerical values within the detailed description and the claims herein are modified by "about" or "approximately" the indicated value, and take into account experimental error and variations that would be expected by a person having ordinary skill in the art.

The invention claimed is:

1. A process for producing a mixed xylenes stream and a $C_{9+}$ aromatic hydrocarbon stream, the process comprising the steps of:

(a) contacting an aromatic hydrocarbon feed with an alkylating agent feed in the presence of an alkylation catalyst under alkylation conditions to produce an alkylated aromatic product stream which comprises said mixed xylenes and of said $C_{9+}$ aromatic hydrocarbons, wherein said aromatic hydrocarbon comprises benzene and/or toluene, said alkylating agent comprises methanol and/or dimethyl ether, said alkylation catalyst comprises a molecular sieve having a Constraint Index in the range from greater than zero up to about 3 and alkylation conditions comprises a temperature of less than 500° C., and wherein the molar ratio of aromatic hydrocarbon feed to alkylating agent feed is in the range of greater than 1:1 to less than 4:1;

(b) recovering streams comprising said mixed xylenes and said $C_{9+}$ aromatic hydrocarbon from said alkylated aromatic product stream;

(c) supplying said mixed xylenes stream to a xylenes isomerization unit to produce para-xylene; and (d) supplying said $C_{9+}$ aromatic hydrocarbon stream to a separation unit to recover at least a $C_9$ aromatic hydrocarbon stream, wherein said $C_9$ aromatic hydrocarbon stream comprises a mixture of trimethylbenzenes and a mixture of ethylmethylbenzenes;

(e) supplying said $C_9$ aromatic hydrocarbon stream to a separation unit to recover a stream comprising said mixture of trimethylbenzenes and/or said stream comprising a mixture of ethylmethylbenzenes; and (f) supplying said stream comprising said mixture of trimethylbenzenes and/or said stream comprising a mixture of ethylmethylbenzenes as motor fuels blending component(s).

2. The process of claim 1, wherein said molecular sieve has a MTW, a BEA*, a FAU or a MOR framework structure.

3. The process of claim 2, wherein said molecular sieve having said MTW framework structure is ZSM-12.

4. The process of claim 1, wherein said alkylated aromatic product stream comprises at least about 75 wt % of said mixed xylenes and/or at least about 21 wt % of said $C_{9+}$ aromatic hydrocarbons, each wt % based on the weight of said alkylated aromatic product stream.

5. The process of claim 2, wherein said molecular sieve having said BEA* framework structure is zeolite Beta.

6. The process of claim 2, wherein said molecular sieve having said FAU framework structure is selected from the group consisting of faujasite, zeolite Y, Ultrastable Y (USY), Dealuminized Y (Deal Y), Rare Earth Y(REY), Ultrahydrophobic Y and mixtures thereof.

7. The process of claim 2, wherein said molecular sieve having said MOR framework structure is selected from the group consisting of natural Mordenite, TEA-Mordenite and mixtures thereof.

8. The process of claim 1, wherein said molecular sieve is selected from the group consisting of ZSM-3, ZSM-4, ZSM-14, ZSM-18, ZSM-20, ZSM-38 and mixtures thereof.

9. The process of claim 1, wherein the alkylation conditions comprise a temperature in the range from 300° C. to 450° C., a pressure in the range from 700 kPa-a to 7000 kPa-a, and a weight hourly space velocity based on the aromatic hydrocarbon feed of 50 $hr^{-1}$ to 0.5 $hr^{-1}$.

10. A process for producing a $C_9$ aromatic hydrocarbon stream and a $C_{10}$ aromatic hydrocarbon stream, the process comprising the steps of:

(a) contacting an aromatic hydrocarbon feed comprising benzene and/or toluene with a feed comprising methanol and/or dimethyl ether in the presence of an alkylation catalyst comprising ZSM-12 under alkylation conditions to produce an alkylated aromatic product stream which comprises said $C_9$ aromatic hydrocarbons and $C_{10}$ aromatic hydrocarbons;

wherein the molar ratio of aromatic hydrocarbon feed to feed comprising methanol is in the range of greater than about 1:1 to about 4:1 and said alkylation conditions comprises a temperature in the range of 300° C. to 450° C., a pressure in the range of from 700 kPa-a to 7000 kPa-a, and a weight hourly space velocity based on the aromatic hydrocarbon feed of 50 $hr^{-1}$ to 0.5 $hr^{-1}$;

(b) separating said alkylated aromatic product stream to recover said $C_9$ aromatic hydrocarbon stream and said $C_{10}$ aromatic hydrocarbon stream, wherein said $C_9$ aromatic hydrocarbon stream comprises a mixture of trimethylbenzenes and a mixture of ethylmethylbenzenes;

(c) supplying said $C_9$ aromatic hydrocarbon stream to a separation unit to recover a stream comprising said mixture of trimethylbenzenes and/or said stream comprising a mixture of ethylmethylbenzenes; and (d) supplying said stream comprising said mixture of trimethylbenzenes and/or said stream comprising a mixture of ethylmethylbenzenes as a motor fuels blending component(s).

11. The process of claim 10, further comprising the step of:
(e) supplying said $C_{10}$ aromatic hydrocarbon stream as a motor fuels blending component(s).

12. The process of claim 10, wherein said mixture of trimethylbenzenes comprises 1,2,4-trimethylbenzene, 1,3,5-trimethylbenzene and 1,2,3-trimethylbenzene.

13. The process of claim 10, further comprising the step of:
(e) supplying said stream comprising said mixture of trimethylbenzenes to said separation unit to recover separate streams comprising 1,2,4-trimethylbenzene, 1,3,5-trimethylbenzene and 1,2,3-trimethylbenzene.

14. The process of claim 13, further comprising the step of:
(f) supplying each of said separate trimethylbenzene streams as a motor fuels blending component.

15. The process of claim 10, wherein said mixture of ethylmethylbenzenes comprises 1-ethyl, 2-methylbenzene and 1-ethyl, 3-methylbenzene.

16. The process of claim 15, further comprising the step of:
(e) supplying said stream comprising said mixture of ethylmethylbenzene to said separation unit to recover separate streams comprising 1-ethyl, 2-methylbenzene and 1-ethyl, 3-methylbenzene.

17. The process of claim 16, further comprising the step of:
(f) supplying each of said separate streams comprising 1-ethyl, 2-methylbenzene and 1-ethyl, 3-methylbenzene as a motor fuels blending component.

18. The process of claim 1, wherein the alkylation catalyst is present in a fixed bed.

19. The process of claim 10, wherein the alkylation catalyst is present in a fixed bed.

* * * * *